US 9,700,401 B2

(12) United States Patent
Fleury et al.

(10) Patent No.: US 9,700,401 B2
(45) Date of Patent: Jul. 11, 2017

(54) STENT WITH ANTI-MIGRATION CONNECTORS

(71) Applicant: Boston Scientific Scimed, Inc., Maple Grove, MN (US)

(72) Inventors: Sean P. Fleury, Brighton, MA (US); Dane T. Seddon, Boston, MA (US); Daniel Ross, Watertown, MN (US); Burns P. Doran, Monticello, MN (US)

(73) Assignee: BOSTON SCIENTIFIC SCIMED, INC., Maple Grove, MN (US)

( * ) Notice: Subject to any disclaimer, the term of this patent is extended or adjusted under 35 U.S.C. 154(b) by 216 days.

(21) Appl. No.: 14/483,967

(22) Filed: Sep. 11, 2014

(65) Prior Publication Data

US 2015/0073529 A1    Mar. 12, 2015

Related U.S. Application Data

(60) Provisional application No. 61/877,116, filed on Sep. 12, 2013.

(51) Int. Cl.
*A61F 2/07*    (2013.01)
*A61F 2/915*    (2013.01)
(Continued)

(52) U.S. Cl.
CPC ............. *A61F 2/07* (2013.01); *A61F 2/848* (2013.01); *A61F 2/915* (2013.01); *A61L 31/10* (2013.01);
(Continued)

(58) Field of Classification Search
CPC ...... A61F 2002/91575; A61F 2002/072; A61F 2002/075; A61F 2002/91508;
(Continued)

(56) References Cited

U.S. PATENT DOCUMENTS 4,994,071 A    2/1991  MacGregor
5,397,355 A *  3/1995  Marin ................... A61F 2/91
                                                    623/1.2
(Continued)

FOREIGN PATENT DOCUMENTS

EP        0 732 088 A2   9/1996
WO      2010124286 A1  10/2010
WO      2012047308 A1   4/2012

*Primary Examiner* — Jocelin Tanner
(74) *Attorney, Agent, or Firm* — Seager, Tufte & Wickhem, LLP (57)    ABSTRACT

An endoprosthesis, such as a stent, having anti-migration features. The endoprosthesis includes an expandable tubular framework including a plurality of strut rows and a plurality of connectors extending across interstices between adjacent strut rows and interconnecting adjacent strut rows. The strut rows have an outer diameter in an expanded state and the connectors extend radially outward beyond the outer diameter of the strut rows in the expanded state. The connectors are configured to engage a wall of a body lumen in the expanded state to inhibit migration of the endoprosthesis in the body lumen. The endoprosthesis may include a polymeric cover covering the strut rows and spanning the interstices between adjacent strut rows, while a space between the connectors and the strut rows to which the connectors are interconnected with is devoid of the polymeric cover to permit tissue ingrowth around the connectors.

6 Claims, 8 Drawing Sheets

(51) Int. Cl.
  *A61F 2/848* (2013.01)
  *A61L 31/10* (2006.01)
  *B05D 1/02* (2006.01)
  *B05D 3/00* (2006.01)

(52) U.S. Cl.
  CPC .............. B05D 1/02 (2013.01); B05D 3/007 (2013.01); *A61F 2002/91558* (2013.01); *A61F 2002/91575* (2013.01); *A61F 2220/0008* (2013.01); *A61F 2230/005* (2013.01); *A61F 2230/0013* (2013.01); *A61F 2240/001* (2013.01); *A61F 2250/0039* (2013.01)

(58) Field of Classification Search
  CPC .. A61F 2002/91516; A61F 2002/91525; A61F 2002/91533; A61F 2002/91541; A61F 2002/9155; A61F 2002/91558; A61F 2002/91566; A61F 2002/8483; A61F 2002/8486; A61F 2/07; A61F 2/848; A61F 2/89; A61F 2/91; A61F 2250/0039; A61F 2230/005; A61F 2230/0013; A61F 2220/0008; A61F 2220/0016; A61F 2240/001; A61L 31/10; B05D 1/02; B05D 3/007
  See application file for complete search history.

(56) References Cited

U.S. PATENT DOCUMENTS

| | | | |
|---|---|---|---|
| 5,591,197 A * | 1/1997 | Orth .................. | A61F 2/07 606/191 |
| 5,674,277 A | 10/1997 | Freitag | |
| 5,814,063 A | 9/1998 | Freitag | |
| 5,948,016 A * | 9/1999 | Jang .................. | A61F 2/91 623/1.11 |
| 6,210,429 B1 | 4/2001 | Vardi et al. | |
| 7,169,178 B1 * | 1/2007 | Santos .................. | A61F 2/91 623/1.42 |
| 7,527,644 B2 | 5/2009 | Mangiardi et al. | |
| 7,547,321 B2 | 6/2009 | Silvestri et al. | |
| 7,604,660 B2 | 10/2009 | Borg et al. | |
| 7,608,099 B2 | 10/2009 | Johnson et al. | |
| 7,637,934 B2 | 12/2009 | Mangiardi et al. | |
| 7,637,942 B2 | 12/2009 | Mangiardi et al. | |
| 7,651,520 B2 | 1/2010 | Fischell et al. | |
| 7,731,654 B2 | 6/2010 | Mangiardi et al. | |
| 7,785,360 B2 | 8/2010 | Freitag | |
| 7,803,180 B2 | 9/2010 | Burpee et al. | |
| 7,806,918 B2 | 10/2010 | Nissl et al. | |
| 7,875,068 B2 | 1/2011 | Mangiardi et al. | |
| 7,887,579 B2 | 2/2011 | Mangiardi et al. | |
| 7,942,921 B2 | 5/2011 | Nissl et al. | |
| 7,959,671 B2 | 6/2011 | Mangiardi et al. | |
| 8,080,053 B2 | 12/2011 | Satasiya et al. | |
| 8,128,679 B2 | 3/2012 | Casey | |
| 8,142,488 B2 | 3/2012 | Reynolds et al. | |
| 8,206,436 B2 | 6/2012 | Mangiardi et al. | |
| 8,262,721 B2 | 9/2012 | Welborn et al. | |
| 8,267,987 B2 | 9/2012 | Johnson et al. | |
| 8,298,277 B2 | 10/2012 | Mangiardi et al. | |
| 8,323,350 B2 | 12/2012 | Nissl | |
| 8,353,946 B2 | 1/2013 | Mangiardi et al. | |
| 8,535,366 B2 | 9/2013 | Mangiardi et al. | |
| 8,535,370 B1 * | 9/2013 | Eckert .................. | A61F 2/07 623/1.13 |
| 8,652,196 B2 | 2/2014 | Nissl | |
| 8,834,558 B2 | 9/2014 | Nissl | |
| 8,926,683 B2 | 1/2015 | Gill et al. | |
| 2002/0123792 A1 * | 9/2002 | Burgermeister .......... | A61F 2/91 623/1.15 |
| 2003/0093143 A1 * | 5/2003 | Zhao .................. | A61F 2/91 623/1.15 |
| 2003/0176911 A1 * | 9/2003 | Iancea .................. | A61F 2/07 623/1.13 |
| 2003/0191517 A1 * | 10/2003 | Osborne .................. | A61F 2/07 623/1.13 |
| 2005/0113903 A1 * | 5/2005 | Rosenthal .................. | A61F 2/90 623/1.15 |
| 2005/0131515 A1 | 6/2005 | Cully et al. | |
| 2007/0005127 A1 | 1/2007 | Boekstegers et al. | |
| 2007/0213810 A1 | 9/2007 | Newhauser et al. | |
| 2009/0187240 A1 | 7/2009 | Clerc et al. | |
| 2009/0248132 A1 | 10/2009 | Bloom et al. | |
| 2009/0306766 A1 * | 12/2009 | McDermott .................. | A61F 2/88 623/1.16 |
| 2010/0286760 A1 | 11/2010 | Beach et al. | |
| 2011/0093059 A1 * | 4/2011 | Fischell .................. | A61F 2/91 623/1.15 |
| 2011/0098801 A1 | 4/2011 | McDermott et al. | |
| 2011/0230957 A1 | 9/2011 | Bonsignore et al. | |
| 2012/0150277 A1 | 6/2012 | Wood et al. | |
| 2012/0310363 A1 | 12/2012 | Gill et al. | |
| 2013/0018215 A1 | 1/2013 | Snider et al. | |
| 2013/0018452 A1 | 1/2013 | Weitzner et al. | |
| 2013/0085565 A1 | 4/2013 | Eller et al. | |
| 2013/0103163 A1 | 4/2013 | Krimsky et al. | |
| 2013/0110253 A1 | 5/2013 | Gill et al. | |
| 2013/0116770 A1 | 5/2013 | Robinson | |
| 2013/0116771 A1 | 5/2013 | Robinson | |
| 2013/0116772 A1 | 5/2013 | Robinson | |
| 2013/0123897 A1 | 5/2013 | Robinson | |
| 2013/0172983 A1 | 7/2013 | Clerc et al. | |
| 2013/0184808 A1 | 7/2013 | Hall et al. | |
| 2013/0184810 A1 | 7/2013 | Hall et al. | |
| 2013/0325141 A1 | 12/2013 | Gill et al. | |
| 2014/0067047 A1 | 3/2014 | Eller et al. | |
| 2014/0079758 A1 | 3/2014 | Hall et al. | |
| 2014/0081414 A1 | 3/2014 | Hall et al. | |
| 2014/0086971 A1 | 3/2014 | Hall et al. | |
| 2014/0248418 A1 | 9/2014 | Eller et al. | |
| 2014/0249619 A1 | 9/2014 | Eller et al. | |
| 2014/0257461 A1 | 9/2014 | Robinson et al. | |
| 2014/0277562 A1 | 9/2014 | Seddon et al. | |
| 2014/0277573 A1 | 9/2014 | Gill et al. | |
| 2015/0148887 A1 | 5/2015 | Beach et al. | |

* cited by examiner

STENT WITH ANTI-MIGRATION CONNECTORS

CROSS-REFERENCE TO RELATED APPLICATIONS

This application claims priority to U.S. Provisional Application Ser. No. 61/877,116, filed Sep. 12, 2013, the entirety of which is incorporated herein by reference.

TECHNICAL FIELD

The disclosure is directed to an endoprosthesis, such as a stent, having anti-migration features. More particularly, the disclosure is directed to a covered stent having anti-migration features permitting tissue ingrowth through select portions of the stent.

BACKGROUND

An endoprosthesis may be configured to be positioned in a body lumen for a variety of medical applications. For example, an endoprosthesis may be used to treat a stenosis in a blood vessel, used to maintain a fluid opening or pathway in the vascular, urinary, biliary, tracheobronchial, esophageal or renal tracts, or to position a device such as an artificial valve or filter within a body lumen, in some instances. Bare or partially covered endoprostheses allow tissue ingrowth through the structure of the endoprosthesis to prevent migration of the endoprosthesis. However, if it is desired to remove the endoprosthesis at some later time, the ingrown tissue must be cut away, causing significant trauma to the body lumen. Fully covered stents, on the other hand, prevent tissue ingrowth to facilitate removal. However, fully covered endoprostheses are prone to migrate through the body lumen.

Accordingly, it is desirable to provide endoprostheses that exhibit anti-migration features, while reducing the trauma to the body lumen of the patient if removal of the endoprosthesis is desired.

SUMMARY

The disclosure is directed to several alternative designs, materials and methods of manufacturing medical device structures and assemblies, and uses thereof.

Accordingly, one illustrative embodiment is an endoprosthesis including an expandable tubular framework having a first end, a second end, and a lumen extending therethrough. The expandable tubular framework includes a plurality of strut rows and a plurality of connectors extending across interstices between adjacent strut rows and interconnecting adjacent strut rows. The expandable tubular framework is expandable from a compressed state to an expanded state. The plurality of strut rows have an outer diameter in the expanded state and the connectors extend radially outward beyond the outer diameter of the plurality of strut rows in the expanded state. The connectors are configured to engage a wall of a body lumen in the expanded state to inhibit migration of the endoprosthesis subsequent implanting the endoprosthesis in the body lumen.

Another illustrative embodiment is an endoprosthesis including an expandable tubular framework having a first end, a second end, and a lumen extending therethrough. The expandable tubular framework is expandable from a compressed state to an expanded state. The expandable tubular framework includes a first strut row, a second strut row, a third strut row, and a fourth strut row. The expandable tubular framework also includes a first plurality of connectors extending across a gap between the first and second strut rows and interconnecting the first and second strut rows, a second plurality of connectors extending across a gap between the second and third strut rows and interconnecting the second and third strut rows, and a third plurality of connectors extending across a gap between the third and fourth strut rows and interconnecting the third and fourth strut rows. The first, second, third and fourth strut rows have an outer diameter in the expanded state, and the first, second and third plurality of connectors extend radially outward in an arcuate pathway beyond the outer diameter of the plurality of strut rows in the expanded state. The first plurality of connectors extends in a first helical direction, the second plurality of connectors extends in a second helical direction opposite the first helical direction, and the third plurality of connectors extends in the first helical direction.

Another illustrative embodiment is a method of manufacturing an endoprosthesis. The method includes forming an expandable tubular framework from a tubular member. The expandable tubular framework has a first end, a second end, and a lumen extending therethrough. The expandable tubular framework includes a plurality of strut rows and a plurality of connectors extending across interstices between adjacent strut rows and interconnecting adjacent strut rows. The expandable tubular framework is coated with a polymeric cover. The coating may then be selectively removed from or prevented from spanning the spaces between the connectors and the strut rows while retaining the coating covering the strut rows and spanning the interstices between adjacent strut rows. For example, fluid may be blown toward spaces between the connectors and the strut rows to which the connectors are interconnected to selectively remove the coating from the spaces while retaining the coating covering the strut rows and spanning the interstices between adjacent strut rows. Alternatively, spray coating processing may be used to selectively remove the coating from the spaces and/or prevent the coating from extending across the spaces while retaining the coating covering the strut rows and spanning the interstices between adjacent strut rows.

Yet another illustrative embodiment is a method of deploying an endoprosthesis in a body lumen. The method includes advancing the endoprosthesis in a compressed state within a tubular sheath to a target location within a body lumen. The endoprosthesis includes an expandable tubular framework having a first end, a second end, and a lumen extending therethrough. The expandable tubular framework is expandable from the compressed state to an expanded state. The expandable tubular framework includes a first strut row, a second strut row, and a third strut row. The expandable tubular framework also includes a first plurality of connectors extending across a gap between the first and second strut rows and interconnecting the first and second strut rows, and a second plurality of connectors extending across a gap between the second and third strut rows and interconnecting the second and third strut rows. The first strut row is expelled from a distal end of the tubular sheath, wherein the first strut row only expands to the expanded state once the entire first strut row is expelled from the tubular sheath while the second and third strut rows remain in the compressed state within the tubular sheath. The second strut row is thereafter expelled from the distal end of the tubular sheath, wherein the second strut row only expands to the expanded state once the entire second strut row is expelled from the tubular sheath while the third strut row remains in the compressed state within the tubular sheath. The third strut row is thereafter expelled from the distal end of the tubular sheath, wherein the third strut row only expands to the expanded state once the entire third strut row is expelled from the tubular sheath.

The above summary of some example embodiments is not intended to describe each disclosed embodiment or every implementation of the aspects of the disclosure.

BRIEF DESCRIPTION OF THE DRAWINGS

The aspects of the disclosure may be more completely understood in consideration of the following detailed description of various embodiments in connection with the accompanying drawings, in which.

While the aspects of the disclosure are amenable to various modifications and alternative forms, specifics thereof have been shown by way of example in the drawings and will be described in detail. It should be understood, however, that the intention is not to limit aspects of the disclosure to the particular embodiments described. On the contrary, the intention is to cover all modifications, equivalents, and alternatives falling within the spirit and scope of the disclosure.

DETAILED DESCRIPTION

For the following defined terms, these definitions shall be applied, unless a different definition is given in the claims or elsewhere in this specification.

All numeric values are herein assumed to be modified by the term "about", whether or not explicitly indicated. The term "about" generally refers to a range of numbers that one of skill in the art would consider equivalent to the recited value (i.e., having the same function or result). In many instances, the term "about" may be indicative as including numbers that are rounded to the nearest significant figure.

The recitation of numerical ranges by endpoints includes all numbers within that range (e.g., 1 to 5 includes 1, 1.5, 2, 2.75, 3, 3.80, 4, and 5).

Although some suitable dimensions, ranges and/or values pertaining to various components, features and/or specifications are disclosed, one of skill in the art, incited by the present disclosure, would understand desired dimensions, ranges and/or values may deviate from those expressly disclosed.

As used in this specification and the appended claims, the singular forms "a", "an", and "the" include plural referents unless the content clearly dictates otherwise. As used in this specification and the appended claims, the term "or" is generally employed in its sense including "and/or" unless the content clearly dictates otherwise.

The following detailed description should be read with reference to the drawings in which similar elements in different drawings are numbered the same. The detailed description and the drawings, which are not necessarily to scale, depict illustrative embodiments and are not intended to limit the scope of the disclosure. The illustrative embodiments depicted are intended only as exemplary. Selected features of any illustrative embodiment may be incorporated into an additional embodiment unless clearly stated to the contrary.

Figure 1:
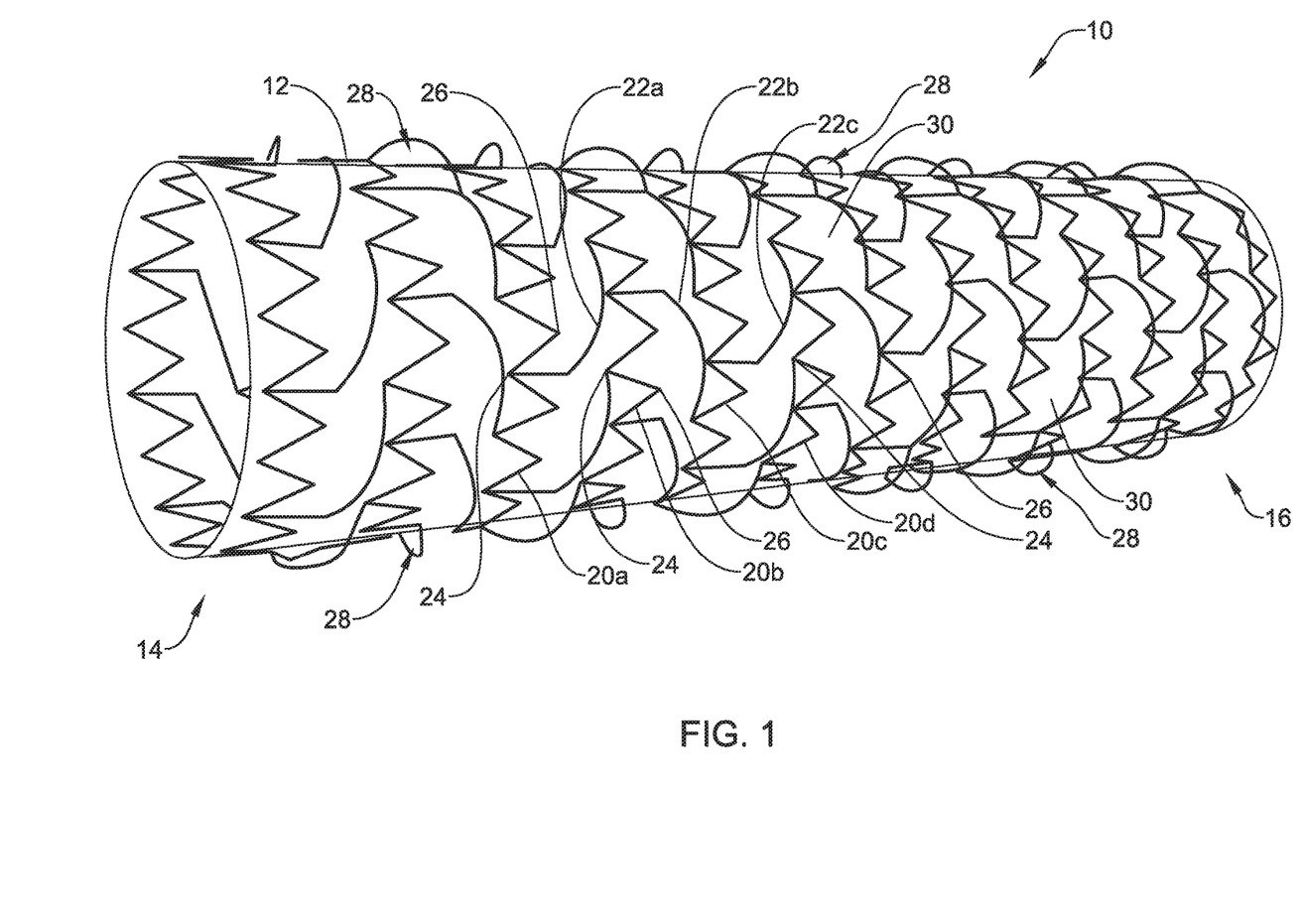
FIG. 1 is a perspective view of an exemplary endoprosthesis.

An exemplary implantable endoprosthesis 10 is shown in FIG. 1. The endoprosthesis 10 may be configured to be positioned in a body lumen for a variety of medical applications. For example, the endoprosthesis 10 may be used to treat a stenosis in a blood vessel, used to maintain a fluid opening or pathway in the vascular, urinary, biliary, tracheobronchial, esophageal or renal tracts, or position a device such as an artificial valve or filter within a body lumen, in some instances. In some instances, the endoprosthesis 10 may be a prosthetic graft, a stent-graft, or a stent (e.g., a vascular stent, tracheal stent, bronchial stent, esophageal stent, etc.). Although illustrated as a stent, the endoprosthesis 10 may be any of a number of devices that may be introduced endoscopically, subcutaneously, percutaneously or surgically to be positioned within an organ, tissue, or lumen, such as a heart, artery, vein, urethra, esophagus, trachea, bronchus, bile duct, or the like.

In some instances, the endoprosthesis 10 may be a self-expandable endoprosthesis configured to automatically expand to an expanded state from a compressed state upon the removal of a constraining force acting on the endoprosthesis. In other instances, the endoprosthesis 10 may be a mechanically expandable endoprosthesis configured to be expanded to an expanded state through the application of a mechanical force acting on the endoprosthesis 10 (e.g., a radially expanding balloon).

The endoprosthesis 10 may be a generally tubular member having an expandable tubular framework 12 extending between a first end 14 and a second end 16, an outer diameter defining an outer surface, and an inner diameter defining an inner surface forming a lumen 18 extending therethrough. The tubular framework 12 may include a plurality of strut rows 20 arranged along the length of the endoprosthesis 10. In some instances, the strut rows 20 may extend circumferentially around a perimeter of the expandable tubular framework 12.

As used herein, the outer surface of the expandable tubular framework 12 is intended to refer to the radially outward facing surface of the strut rows 20 commensurate with the outer diameter of the endoprosthesis 10. As used herein, the inner surface is intended to refer to the radially inward facing surface of the strut rows 20 commensurate with the inner diameter of the endoprosthesis 10.

The expandable framework 12 may include a plurality of strut rows 20 and a plurality of connectors 22 interconnecting adjacent strut rows 20. For example, the expandable framework 12 may include two, three, four, five, six, seven, eight, nine, ten or more strut rows 20 arranged along the length of the endoprosthesis 10. A gap or interstice may be positioned between adjacent strut rows 20 spacing adjacent strut rows 20 apart by the gap or interstice. Thus, the length of the endoprosthesis may be dictated, at least in part, by the number of strut rows 20.

Each strut row 20 may include undulating struts defining interstitial spaces or openings therebetween. The undulating struts of each strut row 20 may include alternating peaks 24 and valleys 26, the peaks 24 and valleys 26 corresponding to where segments of the undulating strut pairs converge and/or diverge. The peaks 24 associated with a strut row 20 are located toward the first end 14 of the tubular expandable framework 12 while the valleys 26 associated with a strut row 20 are located toward the second end 16 of the tubular expandable framework 12.

The endoprosthesis 10 may be formed of any desired material, such as a biocompatible material including biostable, bioabsorbable, biodegradable or bioerodible materials. For instance, the endoprosthesis 10 may be formed of a metallic material or a polymeric material. Some suitable metallic materials include, but are not necessarily limited to, stainless steel, tantalum, tungsten, nickel-titanium alloys such as those possessing shape memory properties commonly referred to as nitinol, nickel-chromium alloys, nickel-chromium-iron alloys, cobalt-chromium-nickel alloys, or other suitable metals, or combinations or alloys thereof. Some suitable polymeric materials include, but are not necessarily limited to, polyamide, polyether block amide, polyethylene, polyethylene terephthalate, polypropylene, polyvinylchloride, polyurethane, polytetrafluoroethylene, polysulfone, and copolymers, blends, mixtures or combinations thereof.

In some instances, the expandable tubular framework 12 of the endoprosthesis 10 may be a monolithic structure formed from a tubular member, such as a metallic tube. For example, the expandable framework 12 may be cut (e.g., laser cut) from a metallic tubular member and then expanded. Thus, the plurality of strut rows 20 and the plurality of connectors 22 of the expandable framework 12 may be formed as a monolithic structure cut from a metallic tube, in some instances. In other instances, the plurality of strut rows 20 and the plurality of connectors 22 of the expandable framework 12 may be cut from a polymeric tubular member. In other embodiments, the expandable framework 12 may be machined, chemically etched, or otherwise formed as a monolithic structure from a tubular member.

Each connector 22 may have a first end connected to a peak 24 in a first strut row 20 and a second end connected to a peak 24 in a second strut row 20 adjacent the first strut row 20. Thus, each connector 22 may extend from a peak 24 in a first strut row 20 to a peak 24 in a second strut row 20. A first plurality of connectors 22a may extend from a first strut row 20a to a second strut row 20b, a second plurality of connectors 22b may extend from the second strut row 20b to a third strut row 20c, a third plurality of connectors 22c may extend from the third strut row 20c to a fourth strut row 20d, etc.

The first plurality of connectors 22a may extend in a first helical direction (e.g., counterclockwise as viewed along the central longitudinal axis of the endoprosthesis 10 toward the second end 16 from the first end 14) from the first strut row 20a to the second strut row 20b. The second plurality of connectors 22b may extend in a second helical direction (e.g., clockwise as viewed along the central longitudinal axis of the endoprosthesis 10 toward the second end 16 from the first end 14), opposite the first helical direction, from the second strut row 20b to the third strut row 20c. The third plurality of connectors 22c may extend in the first helical direction (e.g., counterclockwise as viewed along the central longitudinal axis of the endoprosthesis 10 toward the second end 16 from the first end 14) from the third strut row 20c to the fourth strut row 20d. Thus, the plurality of connectors 22 may alternate helical directions between adjacent strut rows 20 along the length of the endoprosthesis 10. Such an alternative arrangement of the connectors 22 may assist in cancelling twisting or torsional forces imparted on the endoprosthesis 10.

Figure 2:
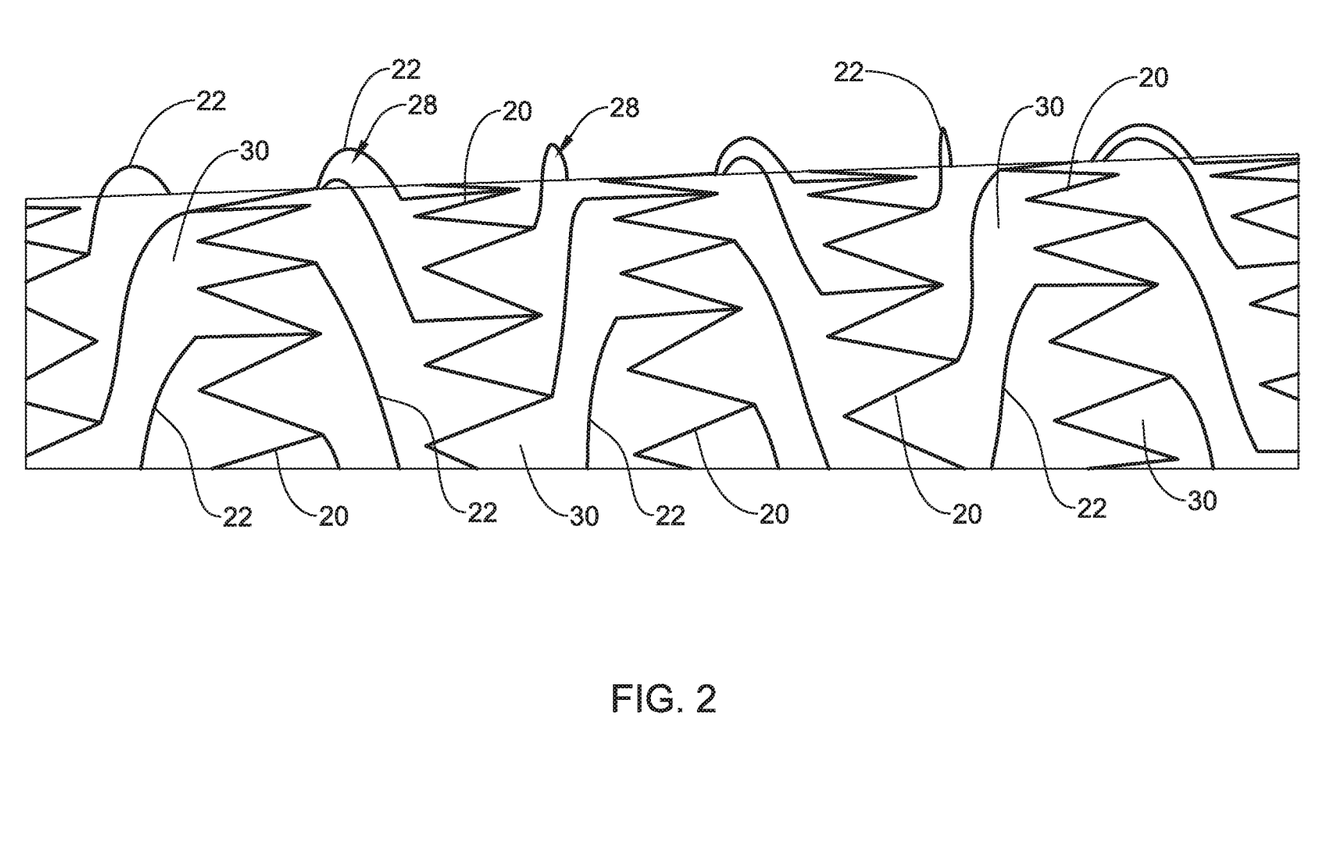
FIG. 2 is an enlarged view of a portion of the endoprosthesis of FIG. 1.
Figure 3:
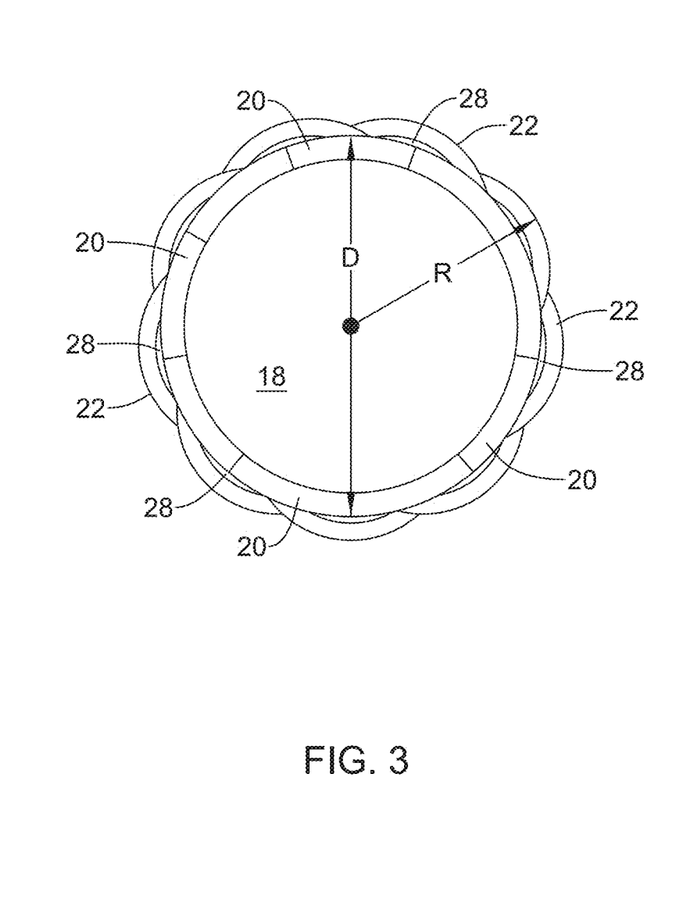
FIG. 3 is an end view of the endoprosthesis of FIG. 1.

Turning to FIGS. 2 and 3, when the endoprosthesis 10 is in the expanded state, the connectors 22 may extend along an arcuate pathway between adjacent strut rows 20 that extends radially outward beyond the outer diameter D of the plurality of strut rows 20 of the expandable framework 12. For example, the connectors 22 may extend a radial distance R from the central longitudinal axis of the endoprosthesis 10, the radial distance R being greater than one-half of the outer diameter D (e.g., the radial distance from the central longitudinal axis to the outward facing surface of the strut rows 20).

The plurality of connectors 22 may be configured to engage a wall of a body lumen in the expanded state to inhibit migration of the endoprosthesis 10 subsequent to implanting the endoprosthesis in the body lumen. For example, the connectors 22 may engage the tissue between cartilage rings within the tracheal anatomy to provide anti-migration support for the endoprosthesis 10.

A space or opening 28 may be defined between the curved or arcuate connectors 22 and the outer diameter D of the strut rows 20 as viewed along the central longitudinal axis of the endoprosthesis 10, as shown in FIG. 3. The space or opening 28 may be unobstructed by any other structure of the endoprosthesis 10. Accordingly, tissue ingrowth through these spaces or openings 28 and covering the connectors 22 subsequent to implanting the endoprosthesis 10 may further secure the endoprosthesis 10 in place in the anatomy and prevent migration of the endoprosthesis 10.

Referring again to FIG. 1, in some embodiments, the endoprosthesis 10 may be covered with a cover 30, such as a polymeric coating. The cover may be any desired polymeric coating, such as a polyurethane coating or silicone coating, for example. In some instances, the cover 30 may include a therapeutic agent, if desired.

In some instances, the endoprosthesis 10, such as a stent, may be considered a fully covered stent in which the cover 30 may extend the full length of the endoprosthesis 10 from the first end 14 to the second end 16. Thus, the cover 30 may cover the strut rows 20 including the interstitial spaces between the strut segments of the strut rows 20 and span the interstices or gaps between adjacent strut rows 20. As shown in FIG. 1, the cover 30 may cover all of the strut rows 20, including the first, second, third and fourth strut rows 20a, 20b, 20c, 20d and span the gaps between the first, second, third and fourth strut rows 20a, 20b, 20c, 20d. In other instances, the endoprosthesis 10, such as a stent, may be considered a partially covered stent in which the cover 30 may extend over a portion of the endoprosthesis 10. For example, the cover 30 may cover one or more of the strut rows 20 including the interstitial spaces between the strut segments of the strut rows 20 and/or span the interstices or gaps between adjacent strut rows 20, but may cover less than all of the plurality of strut rows 20 and/or less than all the interstices or gaps between adjacent strut rows 20.

However, the cover 30 may not extend across the spaces or openings 28 between the curved or arcuate connectors 22 and the strut rows 20. Thus, the space or opening 28 between the connectors 22 and the strut rows 20 to which the connectors 22 are interconnected with may be devoid of the cover 30 to permit tissue ingrowth around the connectors 22 and through the spaces or openings 28. For example, the spaces 28 between the first plurality of connectors 22a and the first and second strut rows 20a, 20b may be devoid of the cover 30 and open (e.g., unobstructed) to permit tissue ingrowth therethrough, the spaces 28 between the second plurality of connectors 22b and the second and third strut rows 20b, 20c may be devoid of the cover 30 and open (e.g., unobstructed) to permit tissue ingrowth therethrough, and the spaces 28 between the third plurality of connectors 22c and the third and fourth strut rows 20c, 20d may be devoid of the cover 30 and open (e.g., unobstructed) to permit tissue ingrowth therethrough. Thus, the endoprosthesis 10 may provide the benefits of a fully covered endoprosthesis, while also providing resistance to migration as a result of tissue ingrowth.

In such an embodiment, the connectors 22 extending between adjacent strut rows 20 may be exposed to permit tissue ingrowth around the connectors 22 and through the spaces or openings 28, while the cover 30 prevents tissue ingrowth around and/or through other portions of the endoprosthesis 10. Accordingly, subsequent to implantation of the endoprosthesis 10, tissue may grow around the connectors 22 and through the spaces or openings 28 to prevent migration of the implanted endoprosthesis 10. However, in the event that it is desired to remove or reposition the endoprosthesis 10 at a subsequent time after tissue ingrowth has occurred, the ingrown tissue can be cut away from the connectors 22 or the connectors 22 can be otherwise released from the ingrown tissue. Since the ingrown tissue is only located at discrete locations (e.g., at the connectors 22), the procedure for removing the endoprosthesis 10 may be less traumatic than if the tissue were ingrown throughout the entire expandable framework 12 including the strut rows 20, such as with a bare endoprosthesis.

Figure 4:
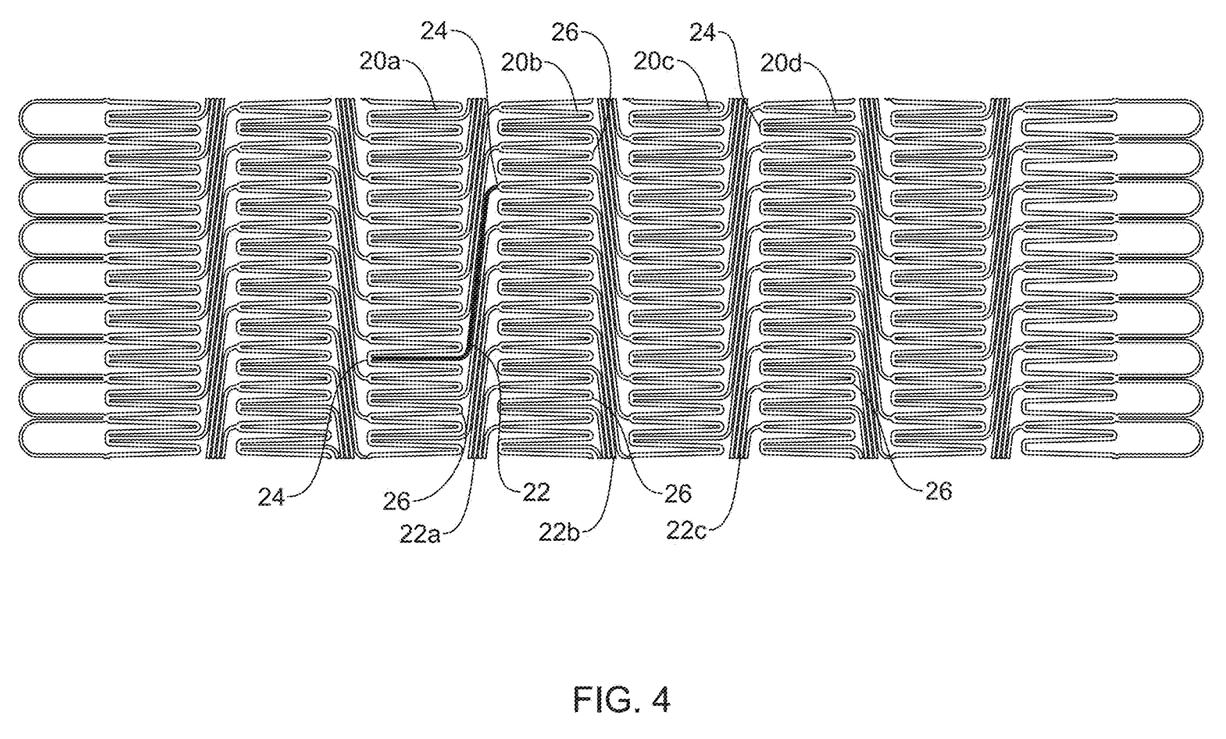
FIG. 4 is a schematic view of the expandable framework of the endoprosthesis of FIG. 1 in a compressed state as if the tubular expandable framework were cut longitudinally and flattened.

As discussed above, in some instances the expandable tubular framework 12 of the endoprosthesis 10 may be formed as a monolithic structure from a metallic tube, such as during a laser cutting process. FIG. 4 is a schematic view of the pattern cut into the metal tube to form the expandable framework 12 of the endoprosthesis of FIG. 1. It is noted that the pattern shown in FIG. 4 is illustrated as if the tubular expandable framework 12 were cut longitudinally and flattened, but one of skill in the art would understand that the pattern would extend circumferentially around the metal tube. As shown in FIG. 4, in the compressed state, the peaks 24 and valleys 26 of the strut rows 20 are closely arranged, and the connectors 22 are arranged in a parallel arrangement at an acute angle from the longitudinal axis of the tubular expandable framework 12 between adjacent strut rows 20. One of the connectors 22 is shaded in FIG. 4 for illustration purposes. The connector 22 may extend from a peak 24 of a first strut row 20a to a peak 24 of a second strut row 20b in a helical fashion, with the end of the connector 22 connected to the first strut row 20a being circumferentially offset from the end of the connector 22 connected to the second strut row 20b. The additional connectors 22 may be similarly arranged. In the compressed state after cutting the pattern in the metal tube, the connectors 22 may be positioned at the same radial distance as the strut rows 20 from the central longitudinal axis of the expandable framework 12.

Figure 5:
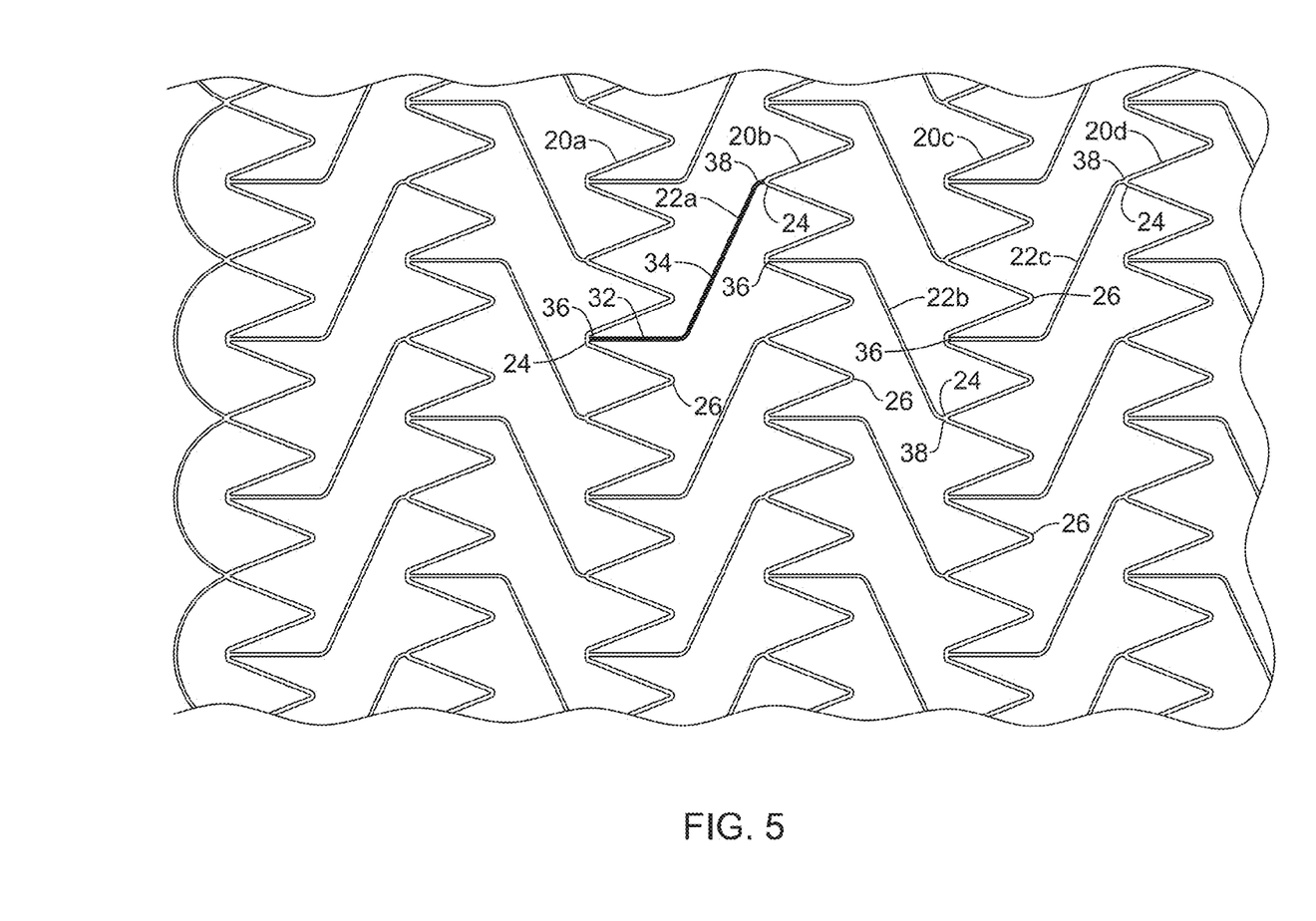
FIG. 5 is a schematic view of the expandable framework of the endoprosthesis in an expanded state.

Once the pattern has been cut into the metal tube, the expandable framework 12 may be expanded from the compressed state in which it was cut from the metal tube to an expanded state. For example, a radially outward force may be applied to the inner surface of the expandable framework 12 to expand the strut rows 20 from a first diameter in the compressed state to a second, enlarged diameter in the expanded state, causing the peaks 24 and valleys 26 of the strut rows 20 to move farther apart. FIG. 5 is an enlarged view of a portion of the pattern of the expandable framework 12 in the expanded state. Furthermore, the acute angle of the connectors 22 from the longitudinal axis of the tubular expandable framework 12 in the expanded state may be less than the acute angle of the connectors 22 in the compressed state.

One of the connectors 22 is shaded in FIG. 5 for illustration purposes. The connector 22 is shown extending from a peak 24 of the first strut row 20a to a peak 24 of the second strut row 20b in a helical fashion, with the first end 32 of the connector 22 connected to the first strut row 20a being circumferentially offset from the second end 34 of the connector 22 connected to the second strut row 20b. A connector 22 of the plurality of connectors 22 extending between the second and third rows 20b, 20c may have a first end connected to a peak 24 of the second strut row 20b and second end connected to a peak 24 of the third strut row 20c, with the first and second ends of the connector 22 being circumferentially offset from each other. The first end of the connector 22 between the second and third rows 20b, 20c may be circumferentially located between the first and second ends 32, 34 of the connector 22 between the first and second rows 20a, 20b. A connector 22 of the plurality of connectors 22 extending between the third and fourth rows 20c, 20d may have a first end connected to a peak 24 of the third strut row 20c and second end connected to a peak 24 of the fourth strut row 20d, with the first and second ends of the connector 22 being circumferentially offset from each other. The first end of the connector 22 between the third and fourth rows 20c, 20d may be circumferentially located between the first and second ends 32, 34 of the connector 22 between the second and third rows 20b, 20c. The additional connectors 22 may be similarly arranged.

As shown in FIGS. 4 and 5, the connectors 22 may include a first end 36 connected to a first strut row 20 and a second end 38 connected to a second strut row 20, adjacent the first strut row 20. The connectors 22 may include a longitudinal segment 32 extending from a peak 24 of the first strut row 20 and an angled segment 34 extending from a peak of the second strut row 20. The longitudinal segment 32 may extend generally parallel to the central longitudinal axis of the tubular expandable framework 12, while the angled segment 34 may extend at an acute angle to the central longitudinal axis of the tubular expandable framework 12.

As the expandable framework 12 is radially expanded to the expanded state, the connectors 22 may extend radially outward from the outer surface of the strut rows 20, such as along a curvilinear or arcuate pathway between adjacent strut rows 20 to which the ends of the connectors 22 are connected to. Accordingly, in the expanded state, the connectors 22 may extend further from the central longitudinal axis of the expandable framework 12 than the strut rows 20 such that the connectors 22 extend above the strut rows 20.

The alternating direction of the helical arrangement of the connectors 22 between adjacent strut rows 20 may reduce and/or eliminate twisting of the expandable framework 12 as the expandable framework 12 is expanded to the expanded state. For example, any twisting between the first and second strut rows 20 in a first direction (e.g., clockwise or counterclockwise) may be offset by counter-twisting between the second and third strut rows 20 in an opposite second direction (e.g., counterclockwise or clockwise).

If it is desired to coat the expandable tubular framework 12 with a polymeric cover 30, the cover 30 may be applied to the expandable tubular framework 12. For example, the expandable tubular framework 12 may be coated with a polymeric cover 30 by dipping the expandable tubular framework 12 into a reservoir of a polymeric material solution. In other instances, the polymeric material may be sprayed onto the expandable tubular framework 12, or otherwise applied to the expandable tubular framework 12.

A layer of the polymeric material solution may be formed across the expandable tubular framework 12, covering the strut rows 20 and spanning the interstices between adjacent strut rows 20, as well as the connectors 22 and the space between the connectors 22 and the strut rows 20 to which the connectors 22 are interconnected. It is noted that the layer of polymeric material solution may be applied to the expandable framework 12 while the expandable framework 12 is positioned around a mandrel.

The expandable framework 12, with a mandrel extending through the lumen of the expandable framework 12, may then be subjected to a process for selectively removing the polymeric material solution from the spaces between the connectors 22 and the strut rows 20 to which the connectors 22 are interconnected while retaining the polymeric material solution covering the strut rows 20 and spanning the interstices between adjacent strut rows 20. For example, a fluid (e.g., air) may be blown toward the spaces 28 between the connectors 22 and the strut rows 20 to selectively remove the coating from the spaces 28. For example, the membrane of the polymeric coating material extending across the spaces 28 may be popped or ruptured by blowing the fluid toward the spaces 28. The fluid (e.g., air) may be directed toward the spaces 28 with one or more fluid nozzles, for example. The presence of the mandrel within the expandable framework 12 may prevent the fluid from rupturing the membrane of the polymeric coating material spanning the interstices between strut rows 20, thus retaining the coating covering the strut rows 20 and spanning the interstices between adjacent strut rows 20. In other instances, the polymeric coating material extending across the spaces 28 may be mechanically popped or ruptured, or the surface tension of the polymeric coating material extending across the spaces 28 may be modified, such as chemically modified, to pop or rupture the polymeric coating material extending across the spaces 28. In other instances, the polymeric coating material may be prevented from spanning the spaces 28 between the connectors 22 and the strut rows 20 while retaining the coating covering the strut rows 20 and spanning the interstices between adjacent strut rows 20. For example, the spaces 28 may be masked off prior to applying the polymeric coating material and then subsequently removed, or the connectors 22 may be pre-treated, such as coated with a material, preventing wetting of the polymeric coating material across the spaces 28 when applying the polymeric coating material.

In some instances, a single layer of the polymeric coating may be applied to form the cover 30. In other instances, multiple layers of the polymeric coating may be applied to form the cover 30. The coating extending across the spaces 28 may be ruptured after each layer of the coating is applied or after multiple layers of the coating have been applied. For example, fluid may be blown toward the spaces 28 to rupture the coating extending across the spaces 28 after each layer of the coating is applied, or after multiple layers of the coating have been applied.

The polymeric material solution coating the expandable framework 12 may then be cured to form the cover 30 disposed on the expandable framework 12. In some instances, the cover 30 may extend the entire length of the expandable framework 12. In other instances, the cover 30 may extend along only a portion of the length of the expandable framework 12, if desired.

In some instances the expandable framework 12 may be configured to match the force required to extend the trachea up to 20% during a cough or deep breath when implanted in the trachea of a patient. The cover 30 increases the force to extend the expandable framework 12 axially, which increases the resistance the endoprosthesis 10 places against the anatomical movements of the trachea. In some embodiments the thickness of the cover 30 may vary at different locations along the length of the expandable framework 12 to reduce the resistance to axial expansion in certain regions of the endoprosthesis 10. For example, in some instances, the cover 30 may have a first thickness throughout a first end region proximate the first end 14 of the expandable framework 12 and/or throughout a second end region proximate the second end 16 of the expandable framework 12, while an intermediate region between the first and second end regions of the expandable framework 12 may have a second thickness different than the first thickness. For example, the second thickness of the cover 30 throughout the intermediate region may be less than the first thickness throughout the first and/or second end regions. In other instances, the second thickness of the cover 30 throughout the intermediate region may be greater than the first thickness throughout the first and/or second end regions.

In one such embodiment, a greater thickness of the cover 30 throughout the first and second end regions of the expandable framework 12 may strengthen the cover 30 in these regions to prevent tearing and/or mucous buildup while implanted in a body lumen. The cover 30 throughout the intermediate region may be thinner to maintain a low axial extension force to prevent migration of the endoprosthesis 10 in the body lumen and enhance patient comfort. Accordingly, the thicker end regions of the cover 30 may have a minimal effect on the overall resistance to axial expansion of the expandable framework 12 since the thicker regions of the cover 30 are located proximate the end regions of the endoprosthesis 10 where tissue ingrowth occurs, while the intermediate region may be configured to prevent tissue ingrowth. Since the endoprosthesis 10 may be anchored to the trachea at the end regions through tissue ingrowth, these end regions would not be susceptible to axial extension as the intermediate region would be.

Figure 6:
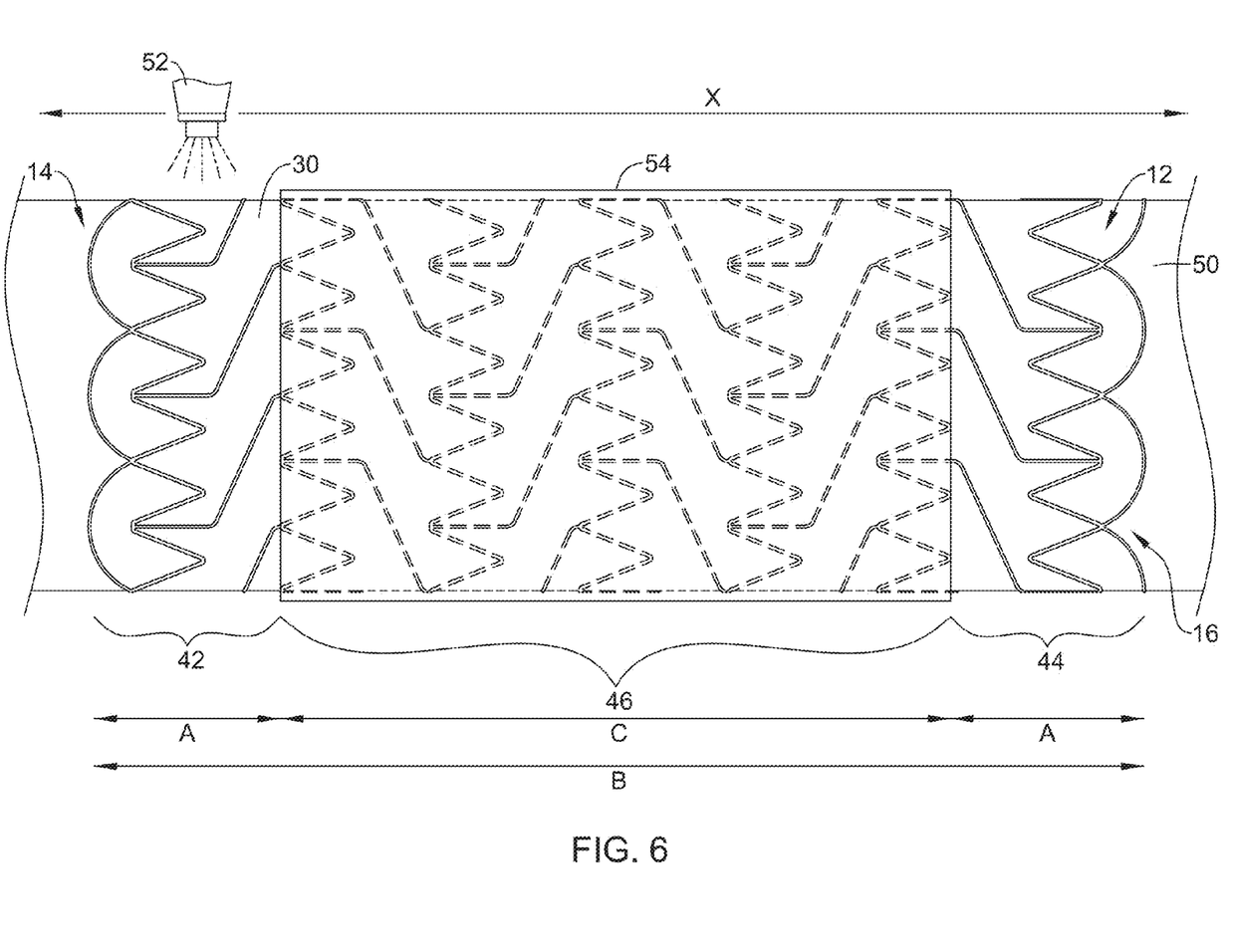
FIG. 6 illustrates an exemplary process of applying a coating to the expandable framework of the endoprosthesis.

FIG. 6 illustrates one possible method of applying a cover 30 having a variable thickness along the expandable framework 12 using a spray coating technique. The illustrated method utilizes a fixture including a nozzle 52 to spray a coating (e.g., a silicone coating) over desired portions of the expandable framework 12.

The expandable framework 12 may be positioned around a mandrel 50 of the fixture. For example, the expandable framework 12 may be disposed on (e.g., surround) the mandrel 50 in an expanded state (e.g., at least partially radially expanded). A protective covering 54 may be positioned over a portion of the expandable framework 12, such as an intermediate region 46 of the expandable framework 12, leaving another portion of the expandable framework 12 exposed (i.e., not covered by the protective covering 54), such as a first end region 42 proximate the first end 14 of the expandable framework 12 and/or a second end region 44 proximate the second end 16 of the expandable framework 12.

The nozzle 52 may be moved axially (shown by arrow X in FIG. 6) along the length of the expandable framework 12, or a portion thereof, to selectively apply one or more layers of a coating on the exposed portions (e.g., the first and second end regions 42, 44) of the expandable framework 12 while the protective covering 54 is positioned over the intermediate region 46. The protective covering 54 may prevent the layers of a coating from being applied to the portion of the expandable framework 12 covered by the protective covering 54. The mandrel 50 may be rotated to rotate the expandable framework 12, and/or the nozzle 52 may move around the circumference of the expandable framework 12, while the nozzle 52 is applying the layers of the coating to apply the coating around the circumference of the expandable framework 12.

After applying one or more layers to the exposed portions (e.g., the first and second end regions 42, 44) of the expandable framework 12, the protective covering 54 may be removed and the nozzle 52 may be moved axially (shown by arrow X in FIG. 6) along the length of the expandable framework 12, or a portion thereof, to selectively apply one or more additional layers of a coating on exposed portions (e.g., the intermediate region 46 and/or the first and second end regions 42, 45) of the expandable framework 12.

The resulting cover 30 applied to the expandable framework 12 may have a first thickness throughout the first end region 42 proximate the first end 14 of the expandable framework 12 and/or throughout the second end region 44 proximate the second end 16 of the expandable framework 12, while the intermediate region 46 between the first and second end regions 42, 44 of the expandable framework 12 may have a second thickness different than the first thickness. The thickness of the cover 30 in the regions may be controlled by the number of layers of the coating applied in the specific region. For example, the second thickness of the cover 30 throughout the intermediate region 46 may be less than the first thickness throughout the first and/or second end regions 42, 44. In other instances, the second thickness of the cover 30 throughout the intermediate region 46 may be greater than the first thickness throughout the first and/or second end regions 42, 44.

In other instances, the expandable framework 12 may be placed on a mandrel 50 in the fixture with or without the protective covering 54. A controller controlling the nozzle 52 may be programmed to apply a polymeric coating to select portions of the expandable framework 12. For example, the nozzle 52 may be programmed to apply one or more layers of a coating along path A and one or more layers of a coating along path B, shown in FIG. 6. Alternatively, the nozzle 52 may be programmed to apply one or more layers of a coating along path A and one or more layers of a coating along path C, shown in FIG. 6. The resulting cover 30 applied to the expandable framework 12 may have a first thickness throughout the first and/or second end regions 42, 44, while the intermediate region 46 may have a second thickness different than the first thickness. The thickness of the cover 30 in the regions may be controlled by the number of layers of the coating applied in the specific region.

In some instances, the controller may be able to adjust the height of the nozzle 52 from the expandable framework 12, speed of the nozzle 52, flow rate of the coating material, and/or rotation of the mandrel 50 incrementally along the expandable framework 12 to effectively apply a different thickness of covering along different portions of the expandable framework 12, as desired.

Figure 7:
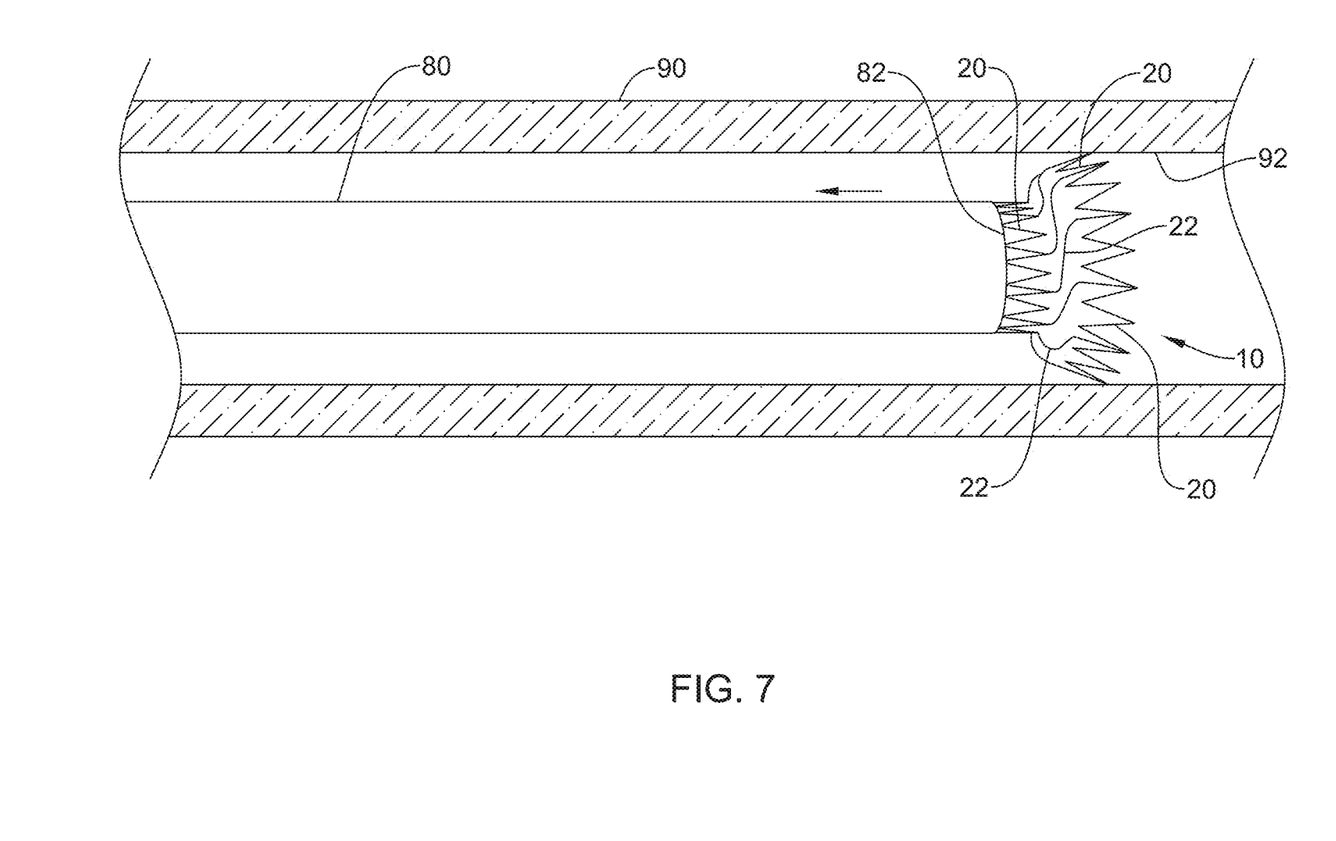
FIGS. 7 and 8 illustrate aspects of delivering the endoprosthesis of FIG. 1 into a body lumen.
Figure 8:
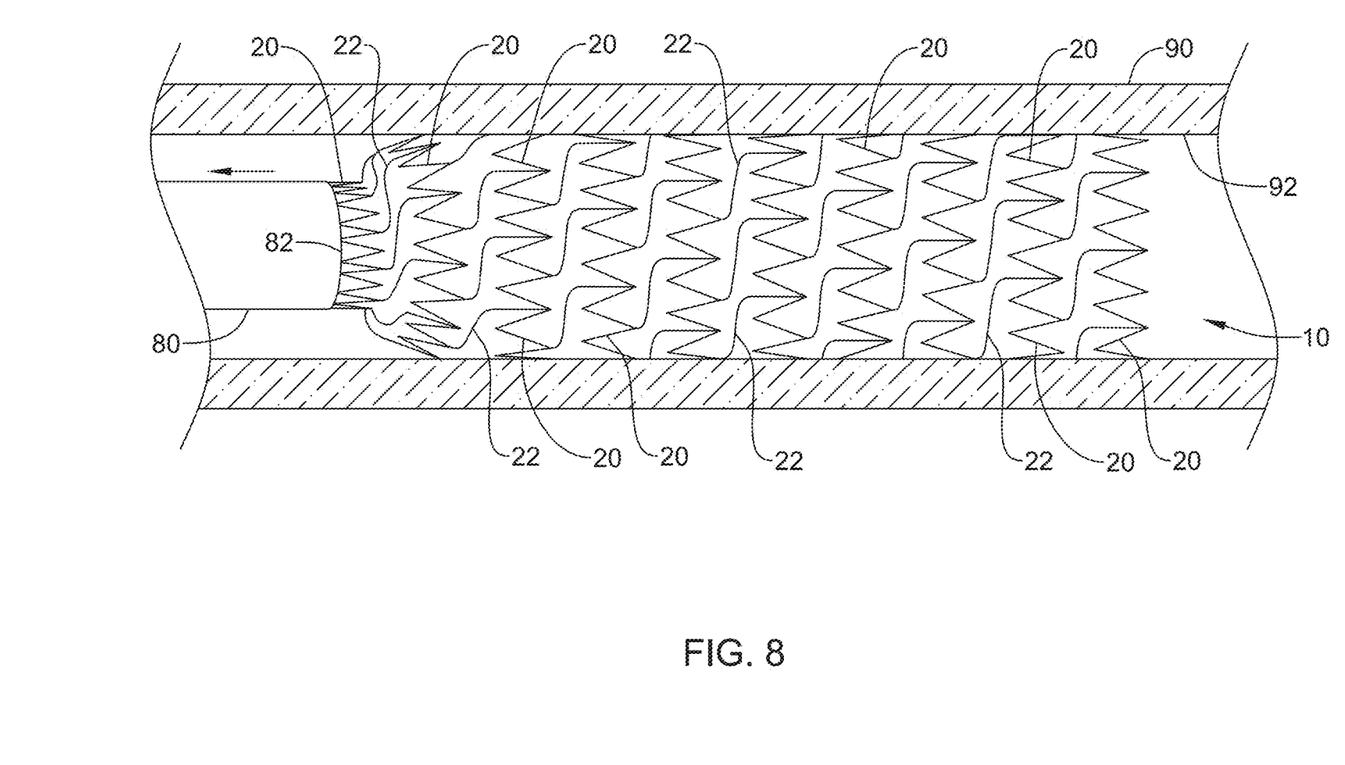

FIGS. 7 and 8 illustrate aspects of delivering the endoprosthesis 10 into a body lumen. As shown in FIG. 7, the endoprosthesis 10 may be advanced in a compressed state within a tubular sheath 80 to a target location within a body lumen 90, such as a body lumen of the vascular, urinary, biliary, tracheobronchial, esophageal or renal tracts. Once positioned at a desired location, the endoprosthesis 10 may be deployed from the distal opening 82 at the distal end of the delivery sheath 80. For example, the delivery sheath 80 may be moved proximally relative to the endoprosthesis 10 such that the endoprosthesis 10 is deployed from the distal opening 82.

The first or distalmost strut row 20 may be expelled from the distal end of the tubular sheath 80, followed by the remainder of the strut rows 20 of the endoprosthesis. As shown in FIG. 7, once a first strut row 20 exits the distal opening 82 of the delivery sheath 80, the first strut row 20 may automatically expand toward its expanded state and press against the luminal wall 92 of the body lumen 90. The connectors 22 may be of sufficient length such that the first strut row 20 may expand against the luminal wall 92 of the body lumen 90 while the adjacent, second strut row 20 may remain in a compressed state within the delivery sheath 80. The first strut row 20 may only expand to the expanded state once the entire first strut row 20 is expelled from the tubular sheath 80.

FIG. 7 illustrates a second strut row 20 emerging from the distal opening 82 of the delivery sheath 80. As shown, the second strut row 20 may remain in the compressed state until the entire strut row 20 is expelled from the tubular sheath 80. The plurality of connectors 22 extending between the first strut row 20 and the second strut row 20 may have a length sufficient to allow the first strut row 20 to fully expand to the expanded state against the luminal wall 92 of the body lumen 90 without expansion of the second strut row 20.

Subsequent strut rows 20 of the endoprosthesis 10, such as third, fourth, fifth, sixth, seventh, eighth and ninth strut rows 20, etc., may be deployed from the delivery sheath 80 in a similar manner. For example, each strut row 20 may remain in the compressed state until the entire strut row 20 is expelled from the distal end of the tubular sheath 80. Thus, each strut row 20 may expand independent of adjacent strut rows 20 and the expansion of a strut row 20 does not cause any jumping effect of adjacent strut rows 20 emerging from the delivery sheath 80.

FIG. 8 illustrates the last or proximalmost strut row 20 of the endoprosthesis 10, just prior to being deployed distal of the delivery sheath 80. Similar to the other strut rows 20, the last or proximalmost strut row 20 strut row 20 may remain in the compressed state until the entire strut row 20 is expelled from the distal end of the tubular sheath 80. Thus, unlike other expandable endoprostheses in which expansion of the endoprosthesis tends to cause adjacent strut rows to "jump" out of the delivery sheath 80 uncontrollably, the endoprosthesis 10 may allow for precise and controlled placement of the endoprosthesis 10 in the body lumen 90.

Furthermore, the stepped deployment of the endoprosthesis 10 may provide tactile feedback to the operator as each strut row 20 is expelled from the distal opening 82 of the delivery sheath 80. For example, a snapping effect or pulse generated at the moment the strut row 20 is fully exposed from the delivery sheath 80 and exits the delivery sheath 80 entirely may translate down the delivery sheath 80 to the operator and may allow the operator to feel when each strut row 20 has expanded in the body lumen 90.

Those skilled in the art will recognize that aspects of the present disclosure may be manifested in a variety of forms other than the specific embodiments described and contemplated herein. Accordingly, departure in form and detail may be made without departing from the scope and spirit of the present disclosure as described in the appended claims.

What is claimed is:
1. An endoprosthesis, comprising:
   an expandable tubular framework having a first end, a second end, and a lumen extending therethrough, the expandable tubular framework being expandable from a compressed state to an expanded state, the expandable tubular framework including:
a first strut row;
a second strut row;
a third strut row;
a fourth strut row;
a first plurality of connectors extending across a gap between the first and second strut rows and interconnecting the first and second strut rows;
a second plurality of connectors extending across a gap between the second and third strut rows and interconnecting the second and third strut rows; and
a third plurality of connectors extending across a gap between the third and fourth strut rows and interconnecting the third and fourth strut rows;
wherein the first, second, third and fourth strut rows have an outer diameter in the expanded state;
wherein the first, second and third plurality of connectors extend radially outward in an arcuate pathway beyond the outer diameter of the plurality of strut rows in the expanded state; and
wherein the first plurality of connectors extends in a first helical direction, the second plurality of connectors extends in a second helical direction opposite the first helical direction, and the third plurality of connectors extends in the first helical direction;
wherein a first end of a first connector of the first plurality of connectors connected to the first strut row is circumferentially offset from a second end of the first connector connected to the second strut row;
wherein a first end of a second connector of the second plurality of connectors connected to the second strut row is circumferentially offset from a second end of the second connector connected to the third strut row; and
wherein the first end of the second connector is circumferentially located between the first and second ends of the first connector.

2. The endoprosthesis of claim 1,
wherein a first end of a third connector of the third plurality of connectors connected to the third strut row is circumferentially offset from a second end of the third connector connected to the fourth strut row; and
wherein the first end of the third connector is circumferentially located between the first and second ends of the second connector.

3. The endoprosthesis of claim 1, further comprising a polymeric cover covering the first, second, third and fourth strut rows and spanning the gaps between the first, second, third and fourth strut rows.

4. The endoprosthesis of claim 3,
wherein radially-extending spaces defined between the first plurality of connectors and an outer diameter of the first and second strut rows as viewed along a central longitudinal axis of the endoprosthesis are devoid of the polymeric cover and open to permit tissue ingrowth therethrough;
wherein radially-extending spaces defined between the second plurality of connectors and an outer diameter of the second and third strut rows as viewed along a central longitudinal axis of the endoprosthesis are devoid of the polymeric cover and open to permit tissue ingrowth therethrough; and
wherein radially-extending spaces defined between the third plurality of connectors and an outer diameter of the third and fourth strut rows as viewed along a central longitudinal axis of the endoprosthesis are devoid of the polymeric cover and open to permit tissue ingrowth therethrough.

5. The endoprosthesis of claim 3, wherein the polymeric cover has a first thickness throughout a first end region of the expandable tubular framework proximate the first end and throughout a second end region of the expandable tubular framework proximate the second end, and the polymeric cover has a second thickness less than the first thickness throughout an intermediate region between the first and second end regions.

6. The endoprosthesis of claim 1, wherein a first end of a first connector of the first plurality of connectors connected to the first strut row is circumferentially offset from a second end of the first connector connected to the second strut row.

* * * * *